US008852906B2

(12) United States Patent
Atkinson et al.

(10) Patent No.: US 8,852,906 B2
(45) Date of Patent: *Oct. 7, 2014

(54) THERMOPHILIC MICRO-ORGANISMS FOR ETHANOL PRODUCTION

(75) Inventors: Anthony Atkinson, Guildford (GB); Roger Cripps, Guildford (GB); Kirstin Eley, Guildford (GB); Brian Rudd, Welwyn Garden (GB); Martin Todd, Welwyn Garden (GB)

(73) Assignee: TMO Renewables Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/357,788

(22) Filed: Jan. 25, 2012

(65) Prior Publication Data

US 2013/0059355 A1    Mar. 7, 2013

Related U.S. Application Data

(63) Continuation of application No. 13/191,056, filed on Jul. 26, 2011, now Pat. No. 8,143,038, which is a continuation of application No. 12/673,399, filed as application No. PCT/GB2008/002782 on Aug. 12, 2008, now Pat. No. 8,021,865.

(30) Foreign Application Priority Data

Aug. 13, 2007 (GB) .................................. 0715751.4

(51) Int. Cl.
*C12P 7/06* (2006.01)
*C12N 9/28* (2006.01)

(52) U.S. Cl.
CPC ............... *C12P 7/065* (2013.01); *Y02E 50/17* (2013.01); *C12N 9/2417* (2013.01)
USPC ......................................................... 435/161

(58) Field of Classification Search
USPC ......................................................... 435/161
See application file for complete search history.

(56) References Cited

U.S. PATENT DOCUMENTS

| | | | |
|---|---|---|---|
| 5,238,833 A | 8/1993 | Sanders et al. | |
| 5,589,369 A | 12/1996 | Seidman et al. | |
| 6,664,076 B2 | 12/2003 | Green et al. | |
| 7,691,620 B2 | 4/2010 | Green et al. | |
| 8,021,865 B2 * | 9/2011 | Atkinson et al. | 435/161 |
| 8,143,038 B2 * | 3/2012 | Atkinson et al. | 435/161 |
| 2002/0034816 A1 | 3/2002 | Green et al. | |
| 2008/0305536 A1 | 12/2008 | Atkinson et al. | |
| 2009/0042265 A1 | 2/2009 | Atkinson et al. | |
| 2009/0197314 A1 | 8/2009 | Atkinson et al. | |
| 2010/0173373 A1 | 7/2010 | Atkinson et al. | |
| 2011/0217760 A1 | 9/2011 | Atkinson et al. | |

FOREIGN PATENT DOCUMENTS

| | | |
|---|---|---|
| EP | 0124076 A2 | 11/1984 |
| EP | 0351717 A2 | 1/1990 |
| EP | 0 937 774 A1 | 8/1999 |
| FR | 2 477 572 A | 9/1981 |
| GB | 2 074 188 A | 8/1981 |
| GB | 2171703 A | 9/1986 |
| JP | 2005-261239 A | 9/2005 |
| WO | WO 88/09379 A2 | 12/1988 |
| WO | WO 98/45425 A1 | 10/1998 |
| WO | WO 01/49865 A1 | 7/2001 |
| WO | WO 01/83784 A2 | 11/2001 |
| WO | WO 02/29030 A2 | 4/2002 |
| WO | WO 2006/117536 A1 | 11/2006 |
| WO | WO 2006/131734 A1 | 12/2006 |
| WO | WO 2007/039753 A1 | 4/2007 |
| WO | WO 2008/038019 A3 | 4/2008 |
| WO | WO 2009/022158 A1 | 2/2009 |
| WO | WO 2010/052499 A1 | 5/2010 |

OTHER PUBLICATIONS

"*Geobacillus*" retrieved from the NCBI Database via http://www.ncbi.nlm.nih.gov/Taxonomy/Browser/wwwtax.cgi?id=129337 on Mar. 22, 2012, 10 pages.
"*Geobacillus* Lactate Dehydrogenase in UniProtKB" retrived from the UnitProt Database via http://www.uniprot.org/uniprot/?query=geobacillus++lactate+dehydrogenase&sort=score on Mar. 22, 2012, 2 pages.
"*Geobacillus* spo0A in UniProtKB" retrieved from the UnitProt Database via http://www.uniprot.org/uniprot/?guery=geobacillus+spo0A&sort=score on Mar. 22, 2012, 3 pages.
Office Action dated Mar. 28, 2012 in U.S. Appl. No. 13/127,927, filed May 13, 2011.
Barstow, D.A. et al. "Cloning, expression and complete nucleotide sequence of the *Bacillus stearothermophilus* L-lactate dehydrogenase gene" *Gene*, 1986, 46:47-55, abstract.
Biswas, I. et al., "High-Efficiency Gene Inactivation and Replacement System for Gram-Positive Bacteria," *Journal of Bacteriology*, Jun. 1, 1993, pp. 175(11):3628-3635, Washington, DC, US, XP000563688.
Breuer, M. et al. "High-throughput assay of (R)-phenylacetylcarbinol synthesized by pyruvate decarboxylase" *Anal Bioanal Chem*, 2002, 374:1069-1073.
Carlsson, J. et al. "Pyruvate Dehydrogenase Activity in *Streptococcus mutans*" *Infection and Immunity*, 1985, 49(3):674-678.
Database WPI Week 200567, Thomson Scientific, AN 2005-653380, XP002487167 & JP2005-261239A, Sep. 29, 2005.
De Graef, M.R. et al. "The Steady-State Internal Redox State (NADH/NAD) Reflects the External Redox State and Is Correlated with Catabolic Adaptation in *Escherichia coli*" *J. Bacteriol.*, Apr. 1999, 181(8):2351-2357.
Desai, S.G. et al., "Cloning of L-lactate dehydrogenase and elimination of lactic acid production via gene knockout in *Thermoanaerobacterium saccharolyticum* JW/SL-Y5485," *Applied Microbiology and Biotechnology*, Oct. 2004, 65(5):600-605, XP002393736.

(Continued)

*Primary Examiner* — Tekchand Saidha
(74) *Attorney, Agent, or Firm* — Saliwanchik, Lloyd & Eisenschenk (57) ABSTRACT

A thermophilic micro-organism comprising a modification that increases amylase expression and starch hydrolysis compared to wild-type, wherein the modification is insertion of a heterologous amylase gene.

19 Claims, 7 Drawing Sheets

(56) References Cited

OTHER PUBLICATIONS

Fong, J.C.N. et al., "Isolation and characterization of two novel ethanol-tolerant facultative-anaerobic thermophilic bacteria strains from waste compost" *Extremophiles*, 2006, 10:363-372.

Fortina, M.G. et al. "Reclassification of *Saccharococcus caldoxylosilyticus* as *Geobacillus caldoxylosilyticus* (Ahmad et al. 2000) comb nov" *International Journal of Systematic and Evolutionary Microbiology*, 2001, 51:2063-2071.

Gao, H. et al. "The E1β and E2 Subunits of the *Bacillus subtilis* Pyruvate Dehydrogenase Complex Are Involved in Regulation of Sporulation" *Journal of Bacteriology*, May 2002, 184(10):2780-2788.

*Geobacillus thermoglucosidasius*. NCBI Databases, pp. 1-3, printed from the internet on Oct. 29, 2010.

Germain, P. et al. "Ethanol production by anaerobic thermophilic bacteria: regulation of lactate dehydrogenase activity in *Clostridium thermohydrosulfuricum*" *Appl Microbial Biotechnol*, 1986, 24:300-305.

Hartley, B.S. et al. (May 1983) "Development and Economics of a Novel Thermophilic Ethanol Fermentation" Presentations from Biotech '83 London, May 4-6, 1983 First World Conference, Biotech, Northwood, Online Conf. LTD, GB, pp. 895-905.

Hollmann, R. et al. "Pyruvate formation and suppression in recombinant *Bacillus megaterium* cultivation" *Journal of Biotechnology*, 2004, 111:89-96.

Jimenez, J. et al. "Selection of Ethanol-Tolerant Yeast Hybrids in pH-Regulated Continuous Culture" *Applied and Environmental Microbiology*, Apr. 1988, 54(4):917-922.

Kuisiene, N. et al, "Phylogenetic, Inter, and Intraspecific Sequence Analysis of spo0A Gene of the Genus *Geobacillus*" *Curr Microbiol*, 2009, 58:547-553.

Lapierre, L. et al. "D-Lactate Dehydrogenase Gene (IdhD) Inactivation and Resulting Metabolic Effects in the *Lactobacillus johnsonii* Strains La1 and N312" *Appl. Environ. Microbiol.*, Sep. 1999, 65(9):4002-4007.

Larsen, L. et al. "*Thermoanaerobacter mathranii* sp. Nov., an ethanol-producing, extremely thermophilic anaerobic bacterium from a hot spring in Iceland" *Arch Microbiol*, 1997, 168:114-119.

Lee, D.H. et al. "Ethanol Fermentation of Corn Starch by a Recombinant *Saccharomyces cerevisiae* Having Glucoamylase and α-Amylase Activities" *J. Food Sci. Nutr.*, 2001, 6(4):206-210.

Lessard, I.A.D. et al. "Expression in *Escherichia coli* of Genes Encoding the E1α and E1β Subunits of the Pyruvate Dehydrogenase Complex of *Bacillus stearothermophilis* and Assembly of a Functional E1 Component (α1 β2) in Vitro" *The Journal of Biological Chemistry*, 1994, 269(14):10378-10383.

Lewis, R.J. et al. "Domain Swapping in the Sporulation Response Regulator Spo0A" *J. Mol. Biol.*, Mar. 31, 2000, 297(3):757-770.

Lynd, L.R. et al. "Thermophilic Ethanol Production: Investigation of Ethanol Yield and Tolerance in Continuous Culture" *Applied Biochemistry and Biotechnology*, 1991, 28/29:549-570.

Molle, V. et al. "The Spo0A regulon of *Bacillus subtilis*" *Molecular Microbiology*, 2003, 50(5):1683-1701.

Nakajima, R. et al. "Nucleotide Sequence of the *Bacillus stearothermophilus* α-Amylase Gene" *J. Bacteriol.*, Jul. 1985, 163(1):401-406.

Neveling, U. et al. "Gene and subunit organization of bacterial pyruvate dehydrogenase complexes" *Biochemica et Biophysica Acta*, 1998, 1385:367-372.

Nichols, N.N. et al. "Engineering lactic acid bacteria with pyruvate decarboxylase and alcohol dehydrogenase genes for ethanol production from *Zymomonas mobilis*" *J Ind Microbiol Biotechnol*, 2003, 30:315-321.

Niu, X.D. et al. "Cloning and nucleotide sequence of the gene for dihydrolipoamide acetyltransferase from *Saccharomyces cerevisiae*" *Proc. Natl. Acad. Sci. USA*, Oct. 1988, 85:7546-7550.

Payton, M.A. "Production of ethanol by thermophilic bacteria," *Trends in Biotechnology*, 1984, 2(6):153-158, Elsevier, Amsterdam, NL, XP000999007.

Rowe-Magnus, D.A. et al. "Identification of a Second Region of the Spo0A Response Regulator of *Bacillus subtilis* Required for Transcription Activation" *J. Bacteriol.*, Aug. 2000, 182(15):4352-4355.

San Martin, R. et al., "Development of a synthetic medium for continuous anaerobic growth and ethanol production with a lactate dehydrogenase mutant of *Bacillus stearothermophilus*," *Journal of General Microbiology*, Feb. 3, 1992, 138:987-996, Great Britain.

San Martin, R. et al., "Pathways of ethanol production from sucrose by a mutant thermophilic *Bacillus* in continuous culture," *Journal of General Microbiology*, Jan. 5, 1993, 139:1033-1040, Great Britain.

Schütz, A. et al. "Crystal structure of thiamindiphosphate-dependent indolepyruvate decarboxylase from *Enterobacter cloacae*, an enzyme involved in the biosynthesis of the plant hormone indole-3-acetic acid" *Eur. J. Biochem.*, 2003, 270:2312-2321.

Schütz, A. et al. "Studies on structure-function relationships of indolepyruvate decarboxylase from *Enterobacter cloacae*, a key enzyme of the indole acetic acid pathway" *Eur. J. Biochem.*, 2003, 270:2322-2331.

Siegert, P. et al. "Exchanging the substrate specificities of pyruvate decarboxylase from *Zymomonas mobilis* and benzoylformate decarboxylase from *Pseudomonas putida*" *Protein Engineering, Design & Selection*, 2005, 18(7):345-357.

Stephenson, K. et al. "Molecular insights into the initiation of sporulation in Gram-positive bacteria: new technologies for an old phenomenon" *FEMS Microbiology Reviews*, 2005, 29:281-301.

Tomar, A. et al. "The effect of acetate pathway mutations on the production of pyruvate in *Escherichia coli*" *Appl Microbiol Biotechnol*, 2003, 62:76-82.

Wendisch, V.F. et al. "Metabolic engineering of *Escherichia coli* and *Corynebacterium glutamicum* for biotechnological production of organic acids and amino acids" *Current Opinion in Microbiology*, 2006, 9:268-274.

Witzmann, S. et al. "The pyruvate dehydrogenase complex from the thermophilic organisms: thermal stability and re-association from the enzyme components" *Biochemica et Biophysica Acta*, 1998, 13885:341-352.

Yomano, L.P. et al. "Isolation and characterization of ethanol-tolerant mutants of *Escherichia coli* KO11 for fuel ethanol production" *Journal of industrial Microbiology & Biotechnology*, Feb. 1998, 20(2):132-138.

Office Action dated May 5, 2010 in U.S. Appl. No. 11/915,930, filed Sep. 29, 2008.

Office Action dated Nov. 15, 2010 in U.S. Appl. No. 11/915,930, filed Sep. 29, 2008.

Office Action dated Nov. 17, 2009 in U.S. Appl. No. 11/913,480, filed Apr. 17, 2008.

Office Action dated Jun. 25, 2010 in U.S. Appl. No. 11/913,480, filed Apr. 17, 2008.

Office Action dated Jun. 16, 2011 in U.S. Appl. No. 12/066,526, filed Jun. 29, 2008.

Office Action dated Mar. 7, 2011 in U.S. Appl. No. 12/376,826, filed May 22, 2009.

Office Action dated Feb. 18, 2011 in U.S. Appl. No. 12/066,526, filed Jun. 29, 2008.

Office Action dated Sep. 15, 2011 in U.S. Appl. No. 13/127,927, filed May 13, 2011.

Office Action dated Sep. 23, 2011 in U.S. Appl. No. 12/376,826, filed May 22, 2009.

* cited by examiner

```
   1 CTAACGTTTCACCGCATCATTCGAAAAGGATGGATGTTCCTGCTCGCGTTTTTGCTCACT
  61 GCCTTGCTGTTCTGCCCAACCGGACAGCCCGCCAAGGCTGCCGCACCGTTTAACGGCACC
 121 ATGATGCAGTATTTTGAATGGTACTTGCCGGATGATGGCACGTTATGGACCAAAGTGGCC
 181 AATGAAGCCAACAACTTATCCAGCCTTGGCATCACCGCTCTTTGGCTGCCGCCCGCTTAT
 241 AAAGGAACAAGCCGCAGCGACGTAGGGTACGGAGTATACGACTTGTATGACCTCGGTGAA
 301 TTCAATCAAAAAGGGGCCGTCCGCACAAAATACGGAACAAAAGCTCAATATCTTCAAGCC
 361 ATTCAAGCCGCCCACGCCGCTGGAATGCAAGTGTACGCCGATGTCGTGTTCGACCATAAA
 421 GGCGGCGCCGACGGCACGGAATGGGTGGACGCCGTCGAAGTCAATCCGTCCGACCGCAAC
 481 CAAGAAATCTCGGGCACCTATCAAATCCAAGCATGGACGAAATTTGATTTTCCCGGGCGG
 541 GGCAACACCTACTCCAGCTTTAAGTGGCGCTGGTACCATTTTGATGGCGTTGATTGGGAC
 601 GAAAGCCGAAAATTGAGCCGCATTTACAAATTCCGCGGCATCGGCAAAGCGTGGGATTGG
 661 GAAGTAGACACGGAAAACGGAAACTATGACTACTTAATGTATGCCGACCTTGATATGGAT
 721 CATCCCGAAGTCGTGACTGAGCTGAAAAGCTGGGGGAAATGGTATGTCAACACAACGAAC
 781 ATTGATGGGTTCCGGCTTGATGCCGTCAAGCATATTAAGTTCAGTTTTTTTCCTGATTGG
 841 TTGTCGTATGTGCGTTCTCAGACTGGCAAGCCGCTATTTACCGTTGGGGAATATTGGAGC
 901 TATAACATCAACAAGTTGCACAATTACATTATGAAAACAAACGGAACGATGTCTTTGTTT
 961 GATGCCCCGTTACACAACAAATTTTATACCGCTTCCAAATCAGGGGGCACATTTGATATG
1021 CGCACGTTAATGACCAATACTCTCATGAAAGATCAACCAACATTGGCCGTCACCTTCGTT
1081 GATAATCATGACACCGAACCCGGCCAAGCGCTGCAGTCATGGGTCGACCCATGGTTCAAA
1141 CCGTTGGCTTACGCCTTTATTCTAACTCGGCAGGAAGGATACCCGTGCGTCTTTTATGGT
1201 GACTATTATGGCATTCCACAATATAACATTCCTTCGCTGAAAAGCAAAATCGATCCGCTC
1261 CTCATCGCGCGCAGGGATTATGCTTACGAACGCAACATGATTATCTTGATCACTCCGAC
1321 ATCATCGGGTGGACAAGGGAAGGGGTCACTGAAAAACCAGGATCCGGACTGGCCGCATTG
1381 ATCACCGATGGGCCGGGAGGAAGCAAATGGATGTACGTTGGCAAACAACACGCCGGAAAA
1441 GTGTTCTACGACCTTACCGGCAACCGGAGTGACACCGTCACCATCAACAGTGATGGATGG
1501 GGGGAATTCAAAGTCAATGGCGGTTCGGTTTCGGTTTGGGTTCCTAGAAAAACGACCGTC
1561 TCTACTATCGCTTGGTCGATCACAACCCGACCGTGGACTGATGAATTCGTCCGTTGGACC
1621 GAACCACGGTTGGTGGCATGGCCTTGATGCCTGC
```

THERMOPHILIC MICRO-ORGANISMS FOR ETHANOL PRODUCTION

CROSS-REFERENCE TO RELATED APPLICATIONS

This application is a continuation of U.S. application Ser. No. 13/191,056, filed Jul. 26, 2011, which is a continuation of U.S. application Ser. No. 12/673,399, filed Apr. 7, 2010, now U.S. Pat. No. 8,021,865, which is the national stage of PCT Application No. PCT/GB2008/002782, filed Aug. 12, 2008, the disclosure of each of which is incorporated herein by reference in its entirety, including all figures, tables, nucleic acid sequences, amino acid sequences, and drawings.

FIELD OF THE INVENTION

This invention relates to the production of micro-organisms suitable for the production of ethanol. In particular, the invention relates to the modification of micro-organisms to enable the utilisation of starch as a fermentation substrate.

BACKGROUND TO THE INVENTION

Bacterial metabolism can occur through various different mechanisms depending on the bacterial species and environmental conditions. Heterotrophic bacteria, which include all pathogens, obtain energy from oxidation of organic compounds, with carbohydrates (particularly glucose), lipids and protein being the most commonly oxidised compounds. Biological oxidation of these organic compounds by bacteria results in synthesis of ATP, a chemical energy source. The process also permits generation of more simple organic compounds (precursor molecules) which are required by the bacterial cell for biosynthetic reactions.

Starch is a naturally abundant carbohydrate and is the principal glucose storage complex in plants. Starch molecules consist of two polysaccharides called amylose and amylopectin. Amylose is a linear polymer of 500 to 20,000 D-glucose subunits, which are linked together via α-1,4 glucosidic bonds to form a helical structure. The additional presence of α-1,6 glucosidic bonds results in amylopectin, which has a branched structure. Starch generally comprises 20-30% amylose and 70-80% amylopectin. In plant cells, insoluble starch is packed into solid granules in which amylopectin is clustered in crystalline regions and amylose is distributed throughout. Starch solubility increases with temperature; amylopectin crystals become gelatinous and granules eventually dissolve.

Amylase is a calcium-dependant glycoside hydrolase metalloenzyme. There are three forms of amylase (α, β and γ) which vary according to the specific bonds they hydrolyse. Alpha-amylase catalyses the random hydrolysis of internal α-D-1,4 glucosidic bonds, releasing simple fermentation sugars including glucose, maltose (disaccharides formed by two glucose units). Dextrins (short, low molecular weight α-1,4-linked D-glucose polymers) are released by amylopectin hydrolysis and maltotriose and maltose are released by amylase hydrolysis. Beta-amylase acts from the non-reducing end of the starch chain, catalysing the hydrolysis of the second α-1,4 glucosidic bond to cleave two glucose units (maltose). Gamma-amylase has the capacity to cleave α-1,6 linkages in amylopectin. Alpha-amylase is widely synthesized in nature since many organisms can digest starch. In human physiology α-amylase is most prominent in saliva and pancreatic secretions. Microbial α-amylases are classified as either liquefying (randomly cleaves the polysaccharide to form shorter chains) or saccharifying (produces mono-, di-, or trisaccharide units), depending on the points of hydrolysis of the glucose polymer chain.

Figure 1:
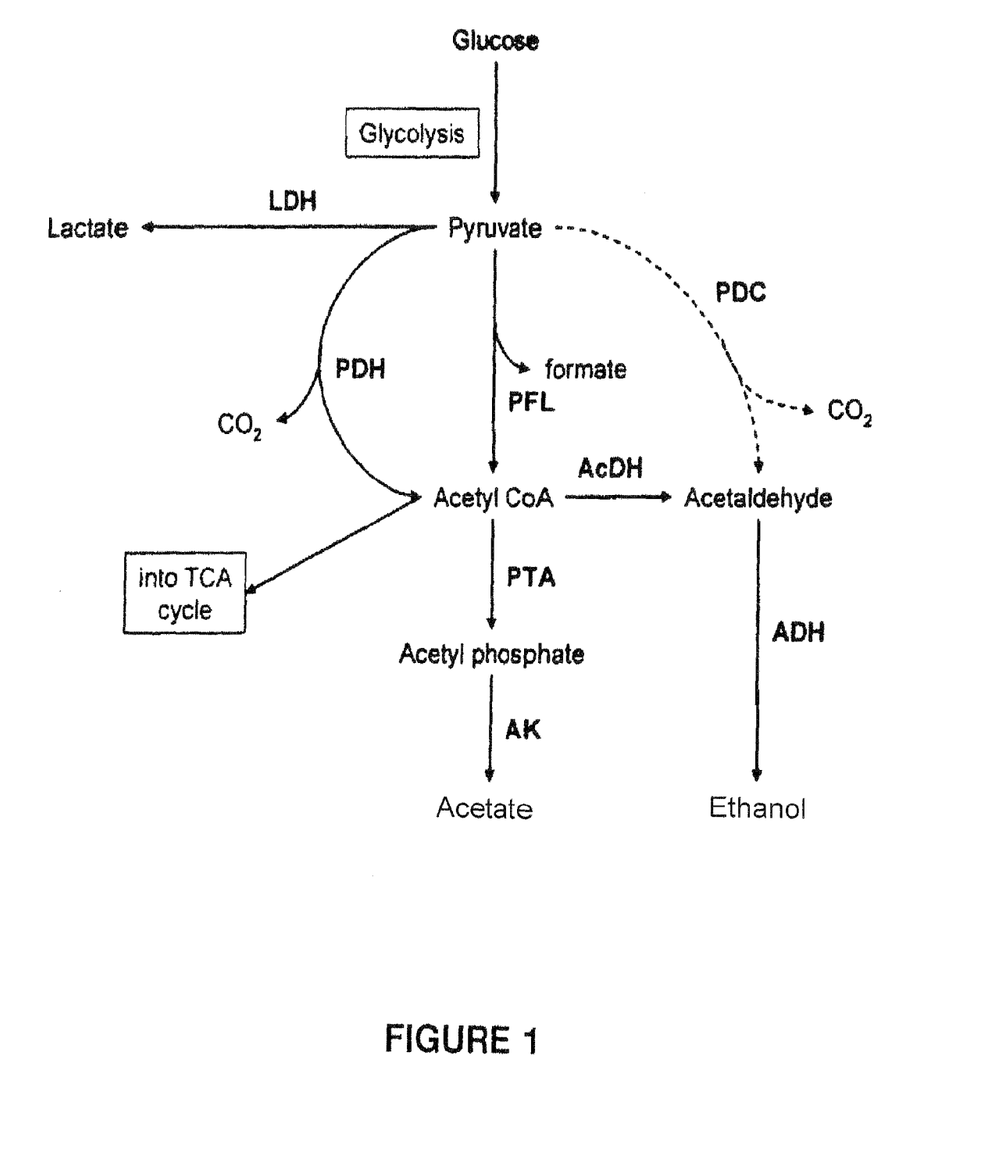
FIG. 1 illustrates schematically the metabolic pathway of glycolysis.

The general process by which bacteria metabolise suitable substrates is glycolysis, which is a sequence of reactions that converts glucose into pyruvate with the generation of ATP. The fate of pyruvate in the generation of metabolic energy varies depending on the micro-organism and the environmental conditions. The four principal reactions of pyruvate are illustrated in FIG. 1.

First, under aerobic conditions, many micro-organisms will generate energy using the citric acid cycle and the conversion of pyruvate into acetyl coenzyme A, catalysed by pyruvate dehydrogenase (PDH).

Second, under anaerobic conditions, certain ethanologenic organisms can carry out alcoholic fermentation by the decarboxylation of pyruvate into acetaldehyde, catalysed by pyruvate decarboxylase (PDC) and the subsequent reduction of acetaldehyde into ethanol by NADH, catalysed by alcohol dehydrogenase (ADH).

A third reaction, which also occurs in anaerobic conditions, is the conversion of pyruvate to acetyl CoA, catalysed by pyruvate formate lyase (PFL). Acetyl CoA is subsequently converted into acetaldehyde by the enzyme acetaldehyde dehydrogenase (AcDH) and ethanol is produced by the reduction of acetaldehyde catalysed by ADH.

A fourth process is the conversion of pyruvate into lactate which occurs through catalysis by lactate dehydrogenase (LDH).

There has been much interest in using micro-organisms for the production of ethanol using either micro-organisms that undergo anaerobic fermentation naturally or through the use of recombinant micro-organisms which incorporate the pyruvate decarboxylase and alcohol dehydrogenase genes. The use of such micro-organisms, modified to enhance utilisation of starch as a metabolic substrate, would enable efficient production of ethanol from cheap, abundant, un-refined plant material.

Thermophilic bacteria have been proposed for ethanol production, and their use has the advantage that fermentation can be carried out at elevated temperatures which allows the possibility that the ethanol produced can be removed as vapour at temperatures above 50° C.; this also permits fermentation to be carried out using high substrate concentrations. However, there is a need for improved micro-organisms for ethanol production from starch-based culture media.

SUMMARY OF THE INVENTION

According to a first aspect of the present invention, a thermophilic micro-organism is modified to increase amylase gene expression compared to wild-type, wherein a first modification is the insertion of a heterologous amylase gene under the control of a suitable promoter, or a series of different promoters.

The micro-organism may be further modified to permit increased production of ethanol, via up-regulation of the native pyruvate dehydrogenase gene and inactivation of the native pyruvate formate lyase and lactate dehydrogenase genes.

The micro-organism of the invention shows increased starch hydrolysis and increased ethanol production compared to wild-type.

According to a second aspect of the present invention, a method for the production of ethanol comprises culturing a micro-organism according to the definition provided above under suitable conditions in the presence of starch.

DESCRIPTION OF THE DRAWINGS

The present invention is described with reference to the accompanying figures, wherein:

FIG. 5 is the nucleic acid coding sequence (SEQ ID NO. 1) of amyS;

DESCRIPTION OF THE INVENTION

The present invention is based on the modification of a thermophilic micro-organism to enable enhanced amylase gene expression.

Increasing expression of the amylase gene enables the micro-organism to hydrolyse starch into glucose monomer units which can then be utilised as glycolytic substrates for the formation of pyruvate and subsequently ethanol. Methods of increasing amylase expression and enzyme activity preferably include the use of strong up-stream promoters to regulate transcription of the gene and incorporation of additional amylase genes that are expressed at a higher frequency than the native amylase gene.

The thermophilic micro-organism of the invention may be further modified to disrupt the expression of the native lactate dehydrogenase gene and to up-regulate the PDH gene.

Inactivating the lactate dehydrogenase gene helps to prevent the breakdown of pyruvate into lactate, and therefore promotes (under appropriate conditions) the breakdown of pyruvate into ethanol using pyruvate decarboxylase and alcohol dehydrogenase. It is preferred if the lactate dehydrogenase gene is disrupted by a deletion within or of the gene.

Up-regulating the PDH gene promotes the conversion of pyruvate into acetyl CoA, which can then be used, under appropriate conditions, to produce acetaldehyde and eventually ethanol using acetaldehyde dehydrogenase. A further advantage of up-regulating PDH is that pyruvate levels, which have an inhibitory effect on glucose uptake and glycolysis, are reduced. This further promotes ethanol production.

The term "strong promoter" is defined herein as a promoter that expresses the corresponding protein to a level greater than 0.5% of the soluble protein in a cell.

The micro-organism may be any thermophilic micro-organism, but it is preferred if the micro-organism is of the *Bacillus* species. In particular, it is preferred if the micro-organism is a wild-type micro-organism of the *Geobacillus* species, in particular *Geobacillus thermoglucosidasius*.

In a preferred embodiment, the micro-organisms selected for modification are said to be "wild-type", i.e. they are not laboratory-produced mutants. The micro-organisms may be isolated from environmental samples expected to contain thermophiles. Isolated wild-type micro-organisms may have limited amylase activity, but insufficient to enable ethanol production when cultured in a media comprising starch as the main carbon source. Isolated wild-type micro-organisms will have the ability to produce ethanol from pyruvate but, unmodified, lactate is likely to be the major fermentation product.

It is preferable that the micro-organism of the invention has certain desirable characteristics which permit the micro-organism to be used in a fermentation process. The micro-organism should preferably have no restriction system, thereby avoiding the need for in vivo methylation. It is preferable if the micro-organism is transformable at a high frequency. Furthermore, the micro-organism should be stable to at least 3% w/v ethanol, preferably at least 5-10% w/v ethanol. The micro-organism should have a growth rate in continuous culture to support dilution rates of $0.3\ h^{-1}$ and above.

The micro-organism will be a thermophile and will grow in the temperature range of 40° C.-85° C. Preferably, the micro-organism will grow within the temperature range 50° C.-70° C. In addition, it is desirable that the micro-organism grows in conditions of pH 7.2 or below, in particular pH 4.5-pH 6.9.

The culture media may preferably comprise at least 1% w/v starch, preferably at least 10% w/v starch, and most preferably at least 20% w/v starch. The starch may be soluble or insoluble (e.g. grain starch). Other preferred components of the culture media may include, but are not limited to those listed in Table 1.

TABLE 1

| Chemical | Vol./L | Final Concentration |
|---|---|---|
| $NaH_2PO_4 \cdot 2H_2O$ | 10 ml | 20 mM |
| $K_2SO_4$ | 20 ml | 10 mM |
| Citric acid•$H_2O$ | 8 ml | 8 mM |
| $MgSO_4 \cdot 7H_2O$ | 20 ml | 5 mM |
| $CaCl_2 \cdot 2H_2O$ | 4 ml | 0.08 mM |
| Sulphate Trace Elements Stock Solution | 5 ml | See Table 2 |
| $Na_2MoO_4 \cdot 2H_2O$ | 0.1 ml | 1.65 µM |
| $(NH_4)_2SO_4$ | 12.5 ml | 25 µM |
| 1% Biotin* | 0.3 ml | 12 µM |
| 40% Glucose** | 3 × 25 ml | 3% w/v |
| Antifoam | 2.5 ml | |

*Prepared by dissolving 0.1 g biotin per 10 ml DMSO
**Final glucose concentration preferably between 1 and 4% w/v Components of sulphate trace elements stock solution are shown in Table 2.

TABLE 2

| Chemical | $gl^{-1}$ (ml) | Final Medium Concentration |
|---|---|---|
| Conc. $H_2SO_4$ | 5.000 | |
| Zn $SO_4 \cdot 7H_2O$ | 1.440 | 25 µM |
| Fe $SO_4 \cdot 7H_2O$ | 5.560 | 100 µM |
| Mn $SO_4 \cdot H_2O$ | 1.690 | 50 µM |
| Cu $SO_4 \cdot 5H_2O$ | 0.250 | 5 µM |
| Co $SO_4 \cdot 7H_2O$ | 0.562 | 10 µM |
| Ni $SO_4 \cdot 6H_2O$ | 0.886 | 16.85 µM |
| $H_3BO_3$ | 0.080 | |
| Deionised $H_2O$ (final vol.) | 1000 ml | |

In a preferred embodiment, a heterologous amylase gene encodes α-amylase (α-1,4-glucan-4-glucanohydrolase, EC 3.2.1.1). It is preferred that the amylase gene is derived from the *Geobacillus* species, in particular *Geobacillus stearothermophilus*.

The coding sequence of α-amylase has been elucidated and the techniques enabling isolation and amplification of the gene are well known in the art. In order to enable the micro-organism of the invention to exhibit increased amylase expression compared to wild-type, it is preferred that the amylase gene is placed under the control of a strong promoter, which operates in low-aeration or anaerobic conditions that favour ethanol production by thermophilic micro-organisms. The promoter is preferably an ldh promoter and may be autologous, but is preferably heterologous, and is most preferably derived from the same species as the amylase gene. Examples of suitable promoters include, but are not limited to, P_ldh from *G. stearothermophilus* NCA1503, P_ferrA from *G. stearothermophilus* DSM13240 and P_pfl from *B. cereus* ATCC14579.

In another embodiment of the invention, a series of different strong promoters is placed upstream of the amylase gene in order to further enhance expression. Examples of suitable strong promoters include, but are not limited to, the glyceraldehyde-3-phosphate promoter (P_GAPDH) and amylase promoter from *G. stearothermophilus* NCA 1503.

The nucleic acid sequence of P_ldh is also known and techniques for cloning and assembling the promoter sequence upstream of the amylase gene are known to the skilled person.

Figure 2:
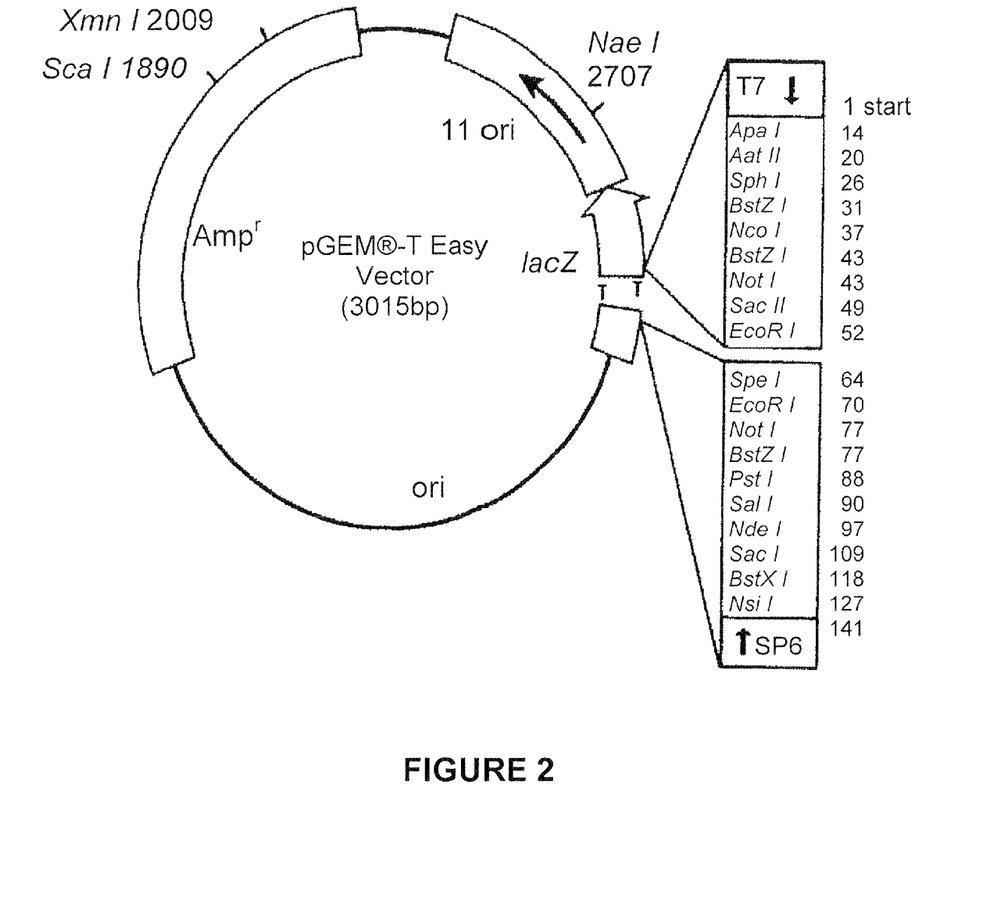
FIG. 2 illustrates the pGEM-T Easy® Vector.

The promoter/amylase sequence can be cloned into a suitable plasmid or expression vector containing multiple restriction sites. There are numerous suitable expression vectors which are commercially available, such as the pGEM®-T Easy Vector (FIG. 2). Restriction enzymes can be used to excise the P_ldh/amylase construct as a specific fragment which can be ligated into the corresponding restriction site in a temperature-sensitive plasmid such as pUC19 (New England Biolabs). It is preferable to use a pyruvate formate lysate knock-out plasmid. The plasmid construct comprising the amylase gene/ldh promoter can then be electroporated into the micro-organism of the invention and achieves homologous recombination with genomic DNA. Chromosomal integrants can be selected for on the basis of their resistance to antibacterial agents, such as ampicillin or kanamycin. Amylase activity can also be visualised as zones of starch clearing, for example on plate assays.

In a preferred embodiment, the micro-organism of the invention is further modified by inactivation of the lactate dehydrogenase gene. The nucleic acid sequence for lactate dehydrogenase is now known. Using this sequence, it is possible for the skilled person to target the lactate dehydrogenase gene to achieve inactivation of the gene through different mechanisms. It is possible to inactivate the lactate dehydrogenase gene by the insertion of a transposon. However, it is preferred if the lactate dehydrogenase gene is inactivated by the deletion of the gene sequence or a portion of the gene sequence. Deletion is preferred as this avoids the difficulty of reactivation of the gene sequence which is often experienced when transposon inactivation is used. In a preferred embodiment, the lactate dehydrogenase gene is inactivated by the integration of a temperature-sensitive plasmid (for example plasmid pUB190-ldh as disclosed in PCT/GB06/01586), which achieves natural homologous recombination or integration between the plasmid and the micro-organism's chromosome. Chromosomal integrants can be selected for on the basis of their resistance to antibacterial agents. The integration into the lactate dehydrogenase gene may occur by a single cross-over recombination event or by a double (or more) cross-over recombination event.

In a further preferred embodiment, the micro-organism is further modified to up-regulate PDH. PDH is a large enzyme complex, containing three units—E1: pyruvate decarboxylase (EC 1.2.4.1, not EC 4.1.1.1), E2: dihydrolipoamide transacetylase, and E3: dihydrolipoamide dehydrogenase. The complex requires several cofactors, including NAD, FAD, coenzyme A lipoic acid and thiamine pyrophosphate (TPP). Four genes code for the complex, as the E1 unit is a heterodimer of α and β subunits, and are often described as pdhA, pdhB, pdhC and pdhD (E1α, E1β, E2 and E3 respectively). The E1 unit of PDH requires TPP in the same way that PDC (EC 4.1.1.1) requires TPP and catalyses a similar decarboxylation reaction, but in the presence of coenzyme A and lipoic acid—carried by other enzyme units—the product is acetyl CoA rather than acetaldehyde. However, PDC activity of the E1 unit has been measured when it has not been complexed with other units in PDH (Lessard & Perham; *The Journal of Biological Chemistry;* 1994, 269:14, 10378-10383; Tomar et al; *Applied Microbiology and Biotechnology;* 2003, 62, 76-82; Frank et al; *Science;* 2004, 306: October 29, 872-876, supplementary data). Accordingly, PDC activity of EC 1.2.4.1 may be enhanced by the up-regulation of PDH so that acetaldehyde is produced over and above acetyl CoA. Enhanced PDH activity is also sought to remove the pyruvate bottleneck observed in LDH inactivated strains to allow more ethanol to be produced with less acetate and formate as side products.

To this end, the PDH genes and surrounding sequence was isolated using standard "genome walking" techniques. Approximately 8.8 kb of DNA was isolated, sequenced and found to contain the following genes shown in FIG. 3 and Table 3.

TABLE 3

Figure 3:
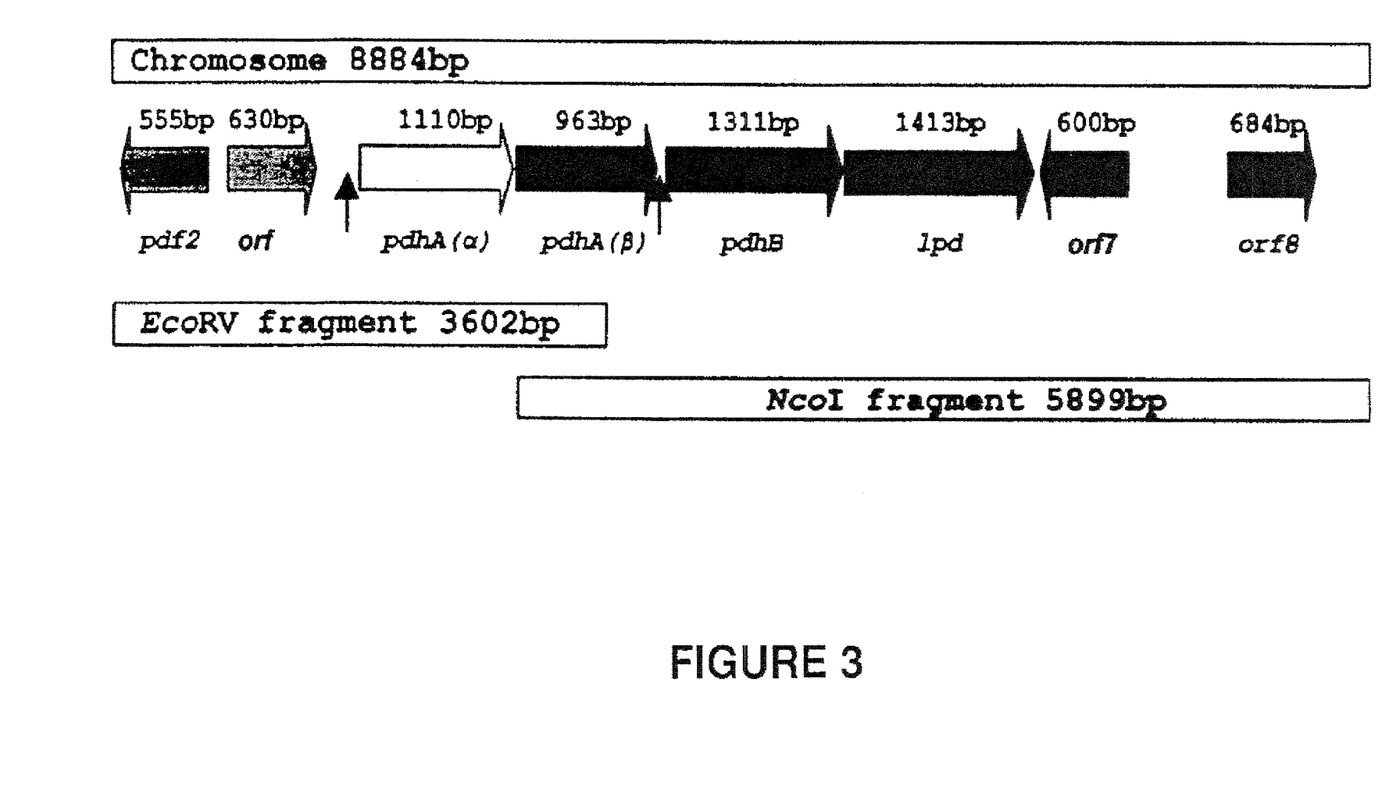
FIG. 3 illustrates the hypothetical promoter regions and genes of the PDH complex.

| Gene | Position (bp) | Proposed function | Frame (aa's at 5' and 3') | Size (aa) |
| --- | --- | --- | --- | --- |
| pdf2 | 746-192 | Peptide deformylase | −3 (MIT-IER) | 184 |
| orf2 | 868-1497 | Unknown-Hypothetical protein | +1 (MQR-IWK) | 209 |
| pdhA(α) | 1875-2984 | α - subunit of pyruvate hydrogenase | +3 (MGA-ESK) | 369 |
| pdh(β) | 3003-3965 | β - subunit of pyruvate dehydrogenase | +3 (MIQ-INF) | 320 |
| pdhB | 4058-5368 | Dihydrolipoamide transacetylase | +2 (VAF-MEA) | 436 |
| lpd | 5373-6785 | Lipoamide dehydrogenase | +3 (MVV-ISK) | 470 |
| orf7 | 7432-6833 | Unknown-Hypothetical protein | −1 (MNK-CTE) | 199 |
| orf8 | 7964-8647 | Transposase | +2 (MDL-SPP) | 227 |

The hypothetical promoter regions are shown in FIG. 3 (arrows)—one upstream from the start of pdhA and a possible second promoter ahead of pdhB. A previous example of a secondary promoter in the PDH cluster was reported for *Bacillus subtilis* (Gao et al; *Journal of Bacteriology,* 2002, 184:10, 2780-2788), but most described PDH gene clusters have just one promoter upstream of the cluster (Neveling et al, *Biochimica Acta;* 1998 1385, 367-372. The upregulation can be carried out using techniques known in the art. In particular, upregulation can be carried out by introducing a suitable promoter or enhancer sequence upstream of the PDH complex.

The enzyme complex is known to work under both aerobic and anaerobic conditions (Carlsson et al; *Infection and Immunity;* 1985, 49:3, 674-678) but it is generally considered to be an aerobic enzyme (Ch 15; *Principles of Biochemistry*; Lehninger, Nelson & Cox; 2$^{nd}$ Ed, Worth Publishers, New York, 1993, p 447) with pyruvate formate lyase (PFL) its anaerobic counterpart. Both enzymes convert pyruvate, formed in glycolysis, to acetyl CoA to feed into the TCA cycle but the cycle only works completely under aerobic conditions. However, as it is desirable to use anaerobic conditions, promoters that operate in anaerobic conditions are preferred for use in the invention. Thus promoters for enzymes believed to work under anaerobic conditions—examples being the LDH promoter (P_ldh from *G. stearothermophilus* NCA1503), the PFL promoters (P_pfl from *B. cereus* ATCC14579, and *G. thermoglucosidasius* NCIMB11955) and ferredoxin promoters (P_ferrA from *G. stearothermophilus* DSM13240)—can be used, as in PCT/GB2007/03699 which is incorporated herein by reference.

In a preferred embodiment, a further modification is introduced to enhance the PDC activity, thereby promoting the conversion of pyruvate to acetaldehyde. This can be carried out by inactivating E2; dihydrolipoamide transacetylase (EC 2.3.1.12). Inactivation can be carried out in a manner similar to the inactivation of LDH, but with the E2 gene as the target for disruption.

In a further embodiment, a micro-organism of the invention comprises a modification to inactivate the pyruvate formate lyase gene, thereby preventing/reducing the conversion of pyruvate to acetyl CoA and formate. Pyruvate formate lyase (PFL) is the "anaerobic counterpart" to pyruvate dehydrogenase (PDH) and converts pyruvate to acetyl CoA and formate (see FIG. 1). While acetyl CoA can be converted to ethanol via acetaldehyde dehydrogenase (AcHD), formate is an undesired side product which has the potential to inhibit growth in ethanolgenic organisms.

PFL was chosen as a target for knockout in order to promote the metabolic flux towards ethanol production and to improve the redox balance of the remaining pathway to ethanol synthesis. An additional advantage of this work was the elimination of formate production. PFL activity can be inactivated via transposon insertion, gene deletion or partial gene deletion to produce a mutant which does not rely on antibiotic selection for the continuation of the altered phenotype. In this embodiment, it is preferred that the micro-organism comprises both the lactate dehydrogenase inactivation and the up-regulation of the pyruvate dehydrogenase, so that, under anaerobic conditions, ethanol production is increased.

In a further preferred embodiment, the micro-organism will also comprise heterologous pyruvate decaroboxylase and alcohol dehydrogenase genes. The expression of these heterologous genes results in the production of enzymes which redirect the metabolism so that ethanol is the primary fermentation product. The genes may be obtained from micro-organisms that typically undergo anaerobic fermentation, including *Zymomonas* species, including *Zymomonas mobilis*.

Methods for the preparation and incorporation of the gene into micro-organisms are known, for example in Ingram et al, *Biotech & BioEng*, 1998; 58 (2+3): 204-214 and U.S. Pat. No. 5,916,787, the content of each being incorporated herein by reference. The gene may be introduced in a plasmid or integrated into the chromosome, as will be appreciated by the skilled person.

The micro-organisms of the invention are cultured using soluble starch as part of the feedstock. The temperature, pH and other growth conditions can be selected based on known culture requirements.

An embodiment of the present invention will now be described, with reference to the accompanying drawings, in the following example. Two approaches for generating integrants of the *G. stearothermophilus* DSM22 α-amylase gene in the genome of *G. thermoglucosidasius* NCIMB 11955 are outlined below. The present invention is exemplified, but not limited, by these methods.

Example

Integration of the Amylase Gene

Approach 1: Fast-Track Strategy Using a NotI Fragment from the Existing Clone, pGEM-LA Using techniques well known in the art, the α-amylase sequence (amyS) was generated by PCR and joined to the ldh promoter (P_ldh) from 11955. This construct was cloned into the commercially available pGEM-T Easy® expression vector, generating pGEM-LA. As shown in FIG. 2, the ligation site in the pGEM-T Easy vector is flanked by multiple restriction sites. It is therefore possible to excise the inserted P_ldh/amylase sequences on a NotI/NotI fragment.

The NotI fragment from pGEM-LA was ligated into the NotI site of the pfl knock-out plasmid construct pTMO111 to generate two sibling plasmid constructs, pTMO139 and pTMO140. These were introduced via electroporation into TM242, a stable PFL-negative 11955 strain. Presumptive integrants were selected at 68° C.

The primary transformants (autonomous plasmids) and primary integrants were tested for amylase production by growth as patches on TGP+0.4% soluble starch plates for 3 days at 60° C., followed by flooding with Gram's iodine solution.

Large zones of clearing (starch hydrolysis) were seen around these strains, comparable to a DSM22 control. TM242 gave a trace of activity in this test, much less than DSM22, indicating some background activity. Sub-culture of primary integrants in liquid media in the absence of kanamycin followed by replication of colonies to TGP_kanamycin was used to identify potential double cross-over mutants (DCOs). A total of 32 kanamycin sensitive colonies were tested for amylase activity on TGP+0.4% soluble starch (3 ml in the wells of 12-well Costar plates, 3 days at 60° C.). None gave large zones, except for the positive control, DSM22. The majority of strains gave traces of clearing, similar to the TM242 control, but 5 showed modest yet significant zones of clearing. Diagnostic PCR was carried out on genomic preparations from 2 of these strains, TM319 and TM320, using degenerate primers bamr66a and bamr72, which were designed based on sequence homology between known *Bacillus* PFL sequences. For both strains, a single PCR product of approximately 3.1 kb was obtained, which on digestion with NotI gave a double bank of approximately 0.6 kb and a band of approximately 2.0 kb. This is consistent with the expected gene replacement/insertion. The controls gave the expected results, approximately 1.7 kb product from 11955 (wild-type) which did not cut with NotI and an approximately 1.3 kb product from TM242 which gave a double bank of approximately 0.6 kb on digestion with NotI. It therefore appears that these strains (TM319 and TM320) represent integration of the amylase construct at the pfl locus.

Approach 2: Generating Amylase Constructs with the P_ldh (NCA) Promoter

Figure 4:
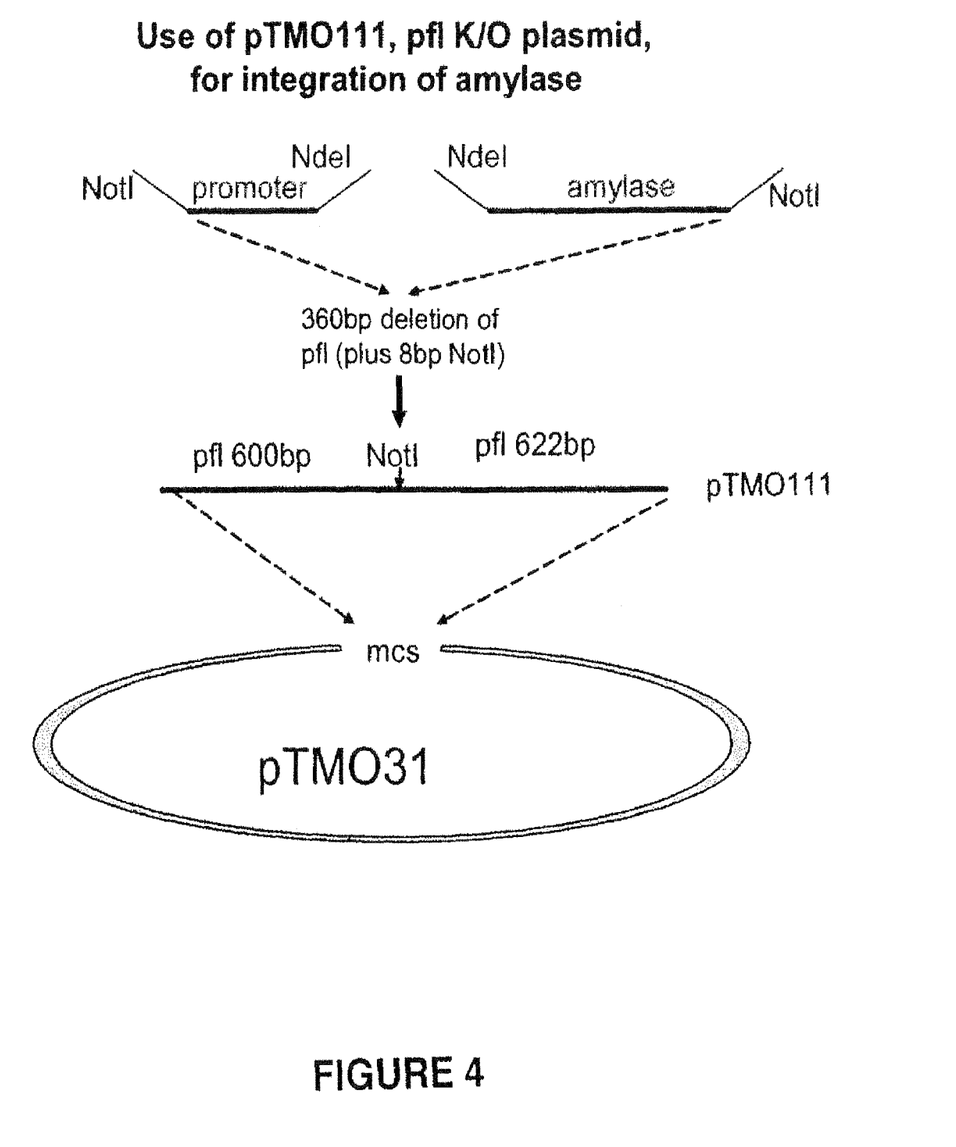
FIG. 4 illustrates the use of pTMO111 for integration of the amylase gene, amyS.

The strategy used to place the amylase coding sequence from DSM22 under the control of P_ldh(NCA) is outlined in FIG. 4. pTMO31 is a plasmid vector comprising ECOR1/SnaB1 pUB110 fragment inserted into the multiple cloning site (mcs) of pUC19 (NEB).

The amylase coding sequence was amplified, via PCR, as an NdeI/NotI fragment, using the pGEM-LA construct as template. P_ldh(NCA) was amplified as a NdeI/NotI fragment using pTMO49 (produced by cloning P_ldh(NCA 1503) into pTMO23) as a template, and the products were cloned and assembled in pTMO23 (pUC19 with NdeI site removed) to generate the insertion (gene replacement) constructs pTMO146 and pTMO147 (sibling plasmids). Table 4 details the PCR components for generation of P_ldh(NCA)/amyS constructs for insertion into 11955.

TABLE 4

| PCR fragment | Template | Primers | Size (bp) |
|---|---|---|---|
| AmyS cds NdeI/NotI | pGEM-LA | Bamr87 Bamr88 | 1657 + primers |

TABLE 4-continued

| PCR fragment | Template | Primers | Size (bp) |
|---|---|---|---|
| P_ldh(NCA) NotI/NdeI | pTMO49 | Bamr89 Bamr38 | 180 + primers |

Sequencing of Amylase Clones

The cloned PCR product for the amylase coding sequence generated using the bamr87 and bamr88 oligos (see Table 4) was sequenced to check integrity. Two independent clones were sequenced. Each showed a different single base-pair mutation, which was presumably introduced by PCR. The clone chosen for progression was pTMO135 (PCR product blunt-end ligated into the SmaI site of pTMO23). The PCR-induced mutation in this clone represents a silent mutation, giving the same amino acid and similar codon usage, as judged by the published codon usage for *G. kaustophilus*. The amylase coding sequence from pTMO135 (omitting the start codon) is shown in FIG. 5. Nucleotides corresponding to discrepancies between this sequence and the published DSM22 amyS sequence (accession number M57457) are underlined. There are 9 differences between the pTMO135 sequence (covering 15 bp) and the published DSM22 amyS sequence (M57457). The mismatch at 1449 represents the PCR-induced mutation in pTMO135.

Sequencing of the amylase insert in pTMO139, which has the NotI fragment from pGEM-LA, showed perfect agreement with pTMO135 (except for the 1449 bp mutation). The amylase coding sequence was then amplified by PCR directly from *G. stearothermophilus* DSM22 genomic DNA (the strain was obtained from the DSMZ collection). The PCR product obtained (using the bamr87 and 88 oligos as before) was cloned into pTMO23 (to give pTMO145) and sequenced. The sequence was identical to pTMO135 (except for the 1449 mutation) and pTMO139, with the exception of bp904. In both pTMO135 and pTMO139 bp904 is "A", but in pTMO145 it is "G". This introduces an aspartic acid to asparagine mutation at this position. This codon (GAO for aspartic acid) proved to be conserved in all *Geobacillus* amylase sequences examined, so it is probably a mutation introduced by PCR cloning of the amylase sequence from DSM22. The other discrepancies in the sequence must be assumed to be errors in the published sequence; alignment with other *Geobacillus* amylase sequences indicates that the sequence (i.e. in pTMO135 and pTMO145) is far closer to the consensus than the published sequence (M57457).

Experimental work continued with the pTMO145 and pTMO146 constructs, despite the 904 mutation, as it was clear that the cloned NotI fragment from pGEM-LA did give substantial amylase activity on starch plates.

Generation and Characterisation of DCOs for pTMO145 and pTMO146 (P_ldh(NCA)/amyS)

pTMO145 and pTMO146 were introduced into TM242 by electroporation and presumptive double cross-over (DCO) mutants were selected as outlined previously. A total of 48 presumptive DCOs (kanamycin-sensitive) were tested in plate assays for amylase activity. 18 gave very strong amylase activity (the others looked similar to the TM242 control). When patched to larger sector plates, they gave zones of clearing at least as large as the DSM22 control. Four of these strains, TM304, TM305, TM311 and TM315, were selected for further work. Genomic DNA was prepared and used in diagnostic PCR. All four gave results indicating insertion of the amyS gene at the pfl locus. Two amylase mutant strains, TM304 and TM305, were tested for ethanol production in ASYE (0.5%) first with glucose as carbon source, and then with soluble starch. Testing was conducted in low and high aeration conditions. The results are shown in Table 5. TM304 and TM305 produce approximately as much ethanol from soluble starch as from glucose in both high and low aeration models. TM242 produces notably lower levels of ethanol on starch compared to glucose, but this effect is considerably less marked in higher aeration conditions. TM304 and TM305 produce similar amounts of ethanol to the TM242 when cultured with glucose, however when the three strains are incubated in the presence of starch it is clear that the superior amylase function of TM304 and TM305 allows the microorganisms to convert substantially all of the starch into ethanol. In low aeration conditions this is almost to the same level as with glucose, whilst TM242's ability to produce ethanol from starch is approximately a third of its ability to convert glucose to ethanol.

TABLE 5

| Strain | Carbon source | O$_2$ | Glucose | Ethanol | Acetate | Starch* |
|---|---|---|---|---|---|---|
| TM304 | 2% glucose | Low | 15.9 | 144.6 | 3.1 | |
| TM305 | 2% glucose | Low | 14.3 | 141.8 | 3.4 | |
| TM242 | 2% glucose | Low | 8.7 | 142.7 | 3.8 | |
| TM304 | 2% soluble starch | Low | 3.8 | 138.4 | 4.1 | |
| TM305 | 2% soluble starch | Low | 4.6 | 135.9 | 3.8 | |
| TM242 | 2% soluble starch | Low | 0.0 | 52.5 | 7.6 | Yes |
| TM304 | 2% glucose | High | 18.2 | 113.4 | 19.7 | |
| TM305 | 2% glucose | High | 10.4 | 119.8 | 20.8 | |
| TM242 | 2% glucose | High | 7.9 | 127.8 | 17.3 | |
| TM304 | 2% soluble starch | High | 16.8 | 98.9 | 20.7 | |
| TM305 | 2% soluble starch | High | 6.7 | 117.9 | 25.2 | |
| TM242 | 2% soluble starch | High | 6.5 | 78.0 | 23.5 | Yes |

Figure 6:
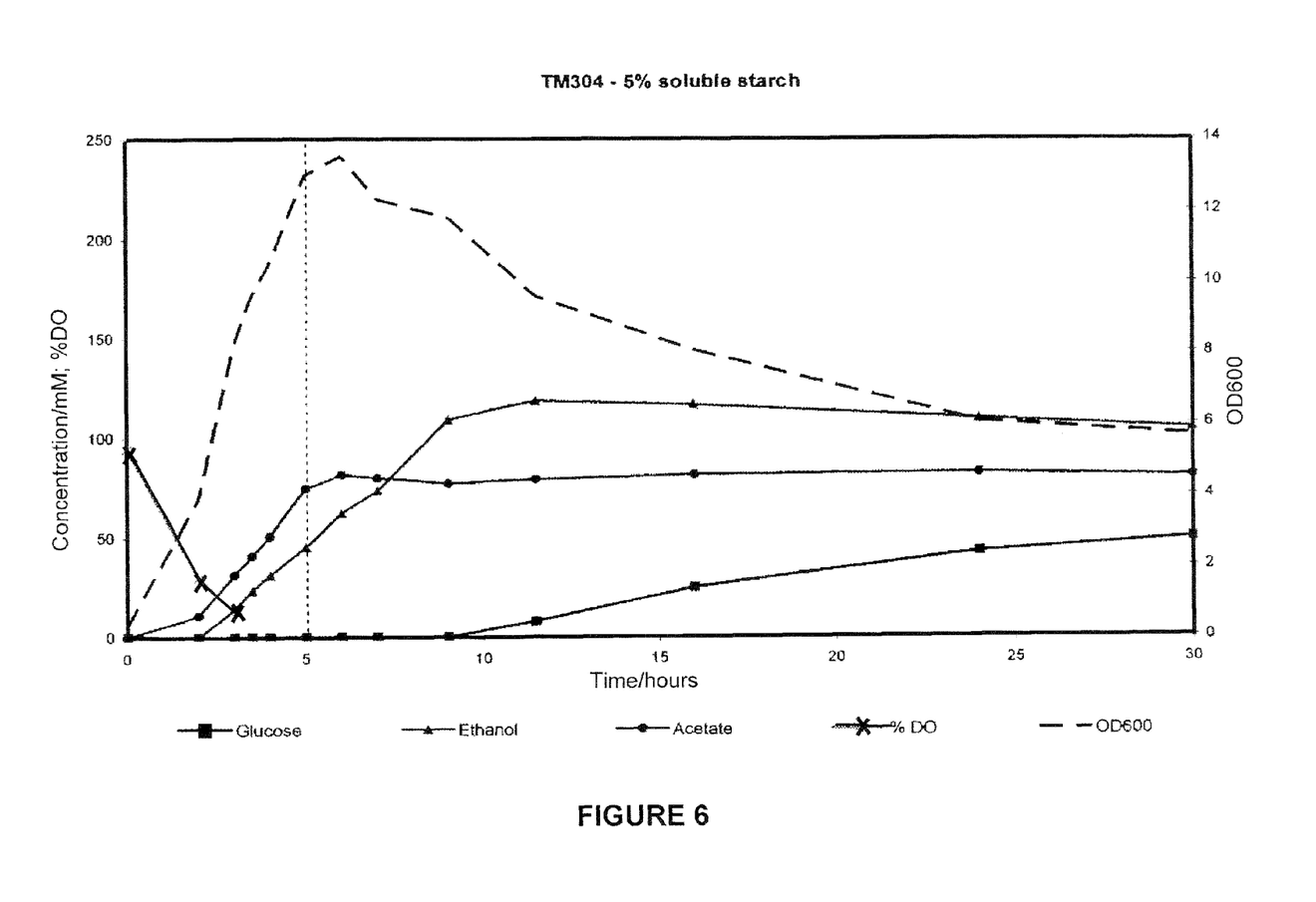
FIG. 6 is a graph showing the batch fermentation results for strain TM304 in a 5% w/v soluble starch culture.

*test for residual starch; 0.5 ml culture plus 0.2 ml Gram's iodine. All negative except those marked.
Inoculum; 100 ul of frozen stock
Seed; 10 ml 2TY in 50 ml conical, 52° C. O/N, 250 rpm, 1 ml transfer (10%)
Production; 10 ml ASYE(0.5%) plus C source in 15 or 50 ml falcon, 60° C., 250 rpm, 24 hrs The batch fermentation results for strain TM304 cultured in 5% w/v soluble starch are shown in FIG. 6. A simple test with Gram's iodine indicated that the DCOs, unlike TM242, hydrolyzed all the starch. The results clearly support the utility of the inserted heterologous amylase under the P_ldh (NCA) promoter for starch utilization in low aeration conditions.

Generation and Characterisation of DCOs for pTMO150 and pTMO151 (P_ldh(NCA)/amyS—No Mutation)

New amyS PCR product from DSM22 genomic DNA was used to generate "clean" DCO constructs, termed pTMO150 and pTMO151. These two plasmids have P_ldh(NCA) inserted into the pfl gene in opposite orientations. pTMO150 is in the same direction of transcription as pfl. pTMO151 is in the opposite direction, as is P_ldh(NCA) in pTMO146 and pTMO147. DCOs were generated from both plasmids and two mutants from each were verified by PCR (TM328 and 329 from pTMO150 and TM333 and 335 from pTMO151). Two amylase mutant strains, TM304 and TM305, were tested. All four mutant strains, together with TM304, TM305 and TM242 were tested for ethanol production in low aeration conditions in ASYE(0.5%), first with 2% w/v glucose as carbon source, and then with 2% w/v soluble starch and finally 3% w/v soluble starch.

The results, which are shown in Table 6, show that all mutant strains performed similarly well in 2% w/v soluble starch, producing over twice as much ethanol as the parent strain TM242. In 3% w/v starch, TM333 produces more ethanol and produces a greater area of clearing on starch plates than the other mutants, indicating that TM333 may be a superior ethanol producer over TM304.

TABLE 6

| Strain | C source | Glucose (mM) | EtOH (mM) | Starch Area |
|---|---|---|---|---|
| TM328 | 2% glucose | 25.1 | 128.6 | 852 |
| TM329 | 2% glucose | 26.7 | 121.3 | 871 |
| TM333 | 2% glucose | 12.7 | 135.4 | 871 |
| TM335 | 2% glucose | 37.5 | 102.8 | 860 |
| TM304 | 2% glucose | 3.9 | 149.8 | 882 |
| TM305 | 2% glucose | 9.5 | 151.5 | 886 |
| TM242 | 2% glucose | 20.4 | 130.8 | 879 |
| TM328 | 2% starch | 5.0 | 127.5 | 1817 |
| TM329 | 2% starch | 4.8 | 132.2 | 1816 |
| TM333 | 2% starch | 4.8 | 133.3 | 1626 |
| TM335 | 2% starch | 12.0 | 124.8 | 1836 |
| TM304 | 2% starch | 6.7 | 135.0 | 1727 |
| TM305 | 2% starch | 6.6 | 136.1 | 1716 |
| TM242 | 2% starch | 0.0 | 62.2 | 3803 |
| TM328 | 3% starch | 13.9 | 139.3 | 2817 |
| TM329 | 3% starch | 14.1 | 137.4 | 2824 |
| TM333 | 3% starch | 30.6 | 151.3 | 2333 |
| TM335 | 3% starch | 16.9 | 121.4 | 2991 |
| TM304 | 3% starch | 31.0 | 141.2 | 2440 |
| TM305 | 3% starch | 30.0 | 140.1 | 2510 |
| TM242 | 3% starch | 0.0 | 75.6 | 6306 |

Figure 7:
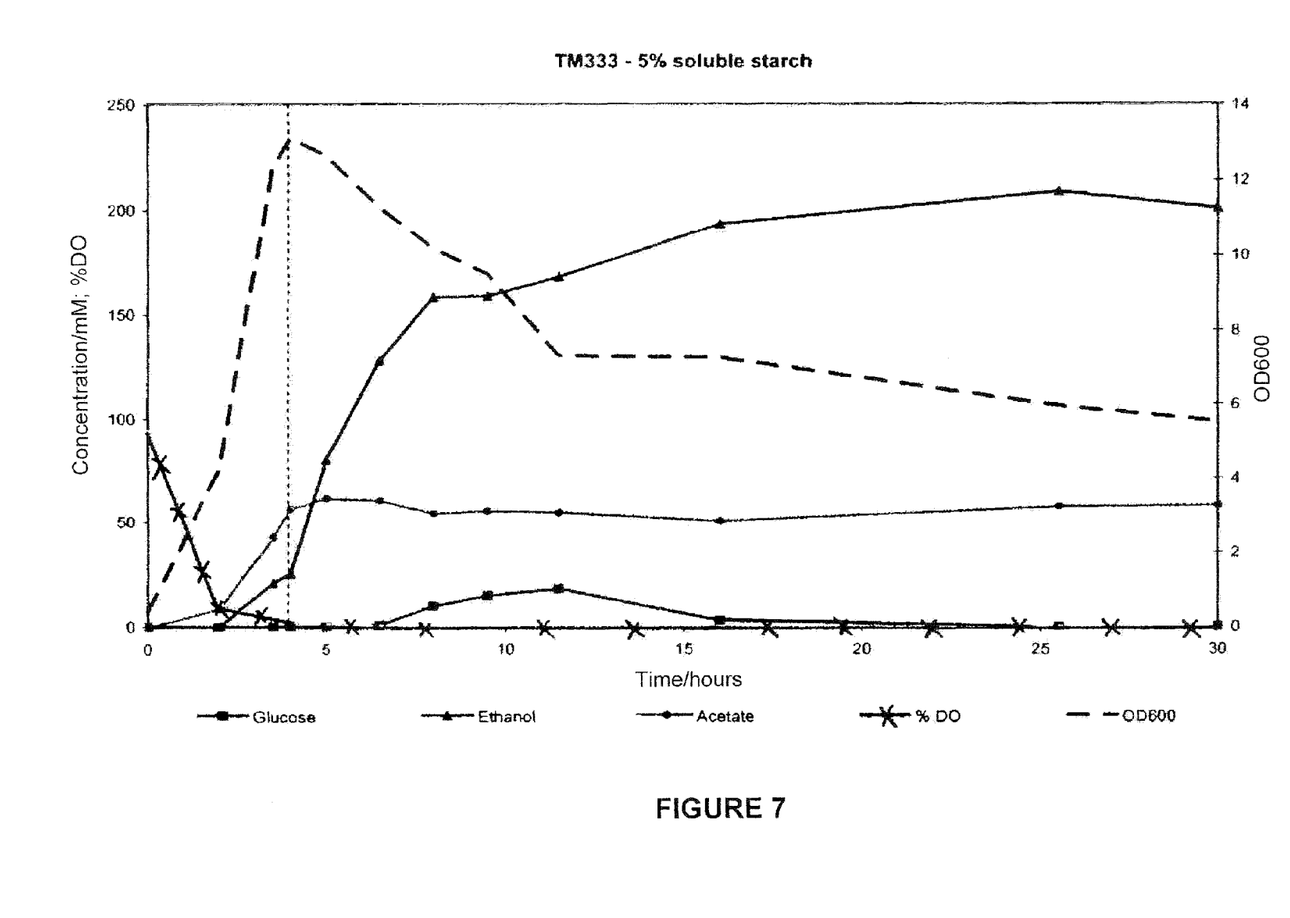
FIG. 7 is a graph showing the batch fermentation results for strain TM333 in a 5% w/v soluble starch culture.

These results are supported by the results of batch fermentation of TM333 (carried out under the same conditions as the fermentation of strain TM304 (FIG. 6)), which are illustrated in FIG. 7 and suggest that TM333 is able to utilise all the glucose released from starch.

Comparative testing was carried out to ensure that the mutant strains TM304 and TM333 performed in a similar fashion to the parent strain TM242 and had not developed any unexpected mutations. The results are shown in Tables 7A and 7B.

TABLE 7A

| Strain | Aeration switch | Hrs to complete sugar consumption | OD | Glucose remaining/ mM | Pyruvate/ mM | Lactate/ mM |
|---|---|---|---|---|---|---|
| TM304 | 3 hr/OD5.9 | 6.2 | 10.1 | 0 | 1 | 8 |
| TM333 | 3 hr/OD5.5 | 7.4 | 9.1 | 0 | 1 | 10 |
| TM242 | 2.5 hr/OD5.6 | 7.5 | 9.8 | 0 | 1 | 10 |

TABLE 7B

| Strain | Formate/ mM | Acetate/ mM | Ethanol/ mM | Ethanol yield post anaerobic switch g/g | Overall ethanol yield: peak ethanol |
|---|---|---|---|---|---|
| TM304 | 0 | 12 | 336 | 0.41 | 0.40 |
| TM333 | 0 | 16 | 293 | 0.44 | 0.38 |
| TM242 | 0 | 13 | 314 | 0.44 | 0.42 |

---

We claim:

1. A thermophilic micro-organism modified by the insertion of a heterologous amylase gene under the control of a suitable promoter, and further modified to inactivate the native lactate dehydrogenase (ldh) gene by deletion of the ldh gene or a portion thereof.

2. The micro-organism according to claim 1, wherein the promoter operates in low aeration or anaerobic conditions.

3. The micro-organism according to claim 1, wherein the promoter is a heterologous ldh promoter.

4. The micro-organism according to claim 3, wherein the ldh promoter is derived from *Geobacillus stearothermophilus*.

5. The micro-organism according to claim 1, wherein the amylase gene is under the control of a series of strong promoters including a glyceraldehyde-3-phosphate dehydrogenase promoter or an amylase promoter.

6. The micro-organism according to claim 5, wherein the promoters are derived from *G. stearothermophilus*.

7. The micro-organism according to claim 1, wherein the micro-organism does not comprise an insertion element in the lactate dehydrogenase gene.

8. The micro-organism according to claim 1, wherein a further modification inactivates the native pyruvate formate lyase gene.

9. The micro-organism according to claim 1, further comprising a modification that up-regulates pyruvate decarboxylase activity.

10. The micro-organism according to claim 1, wherein the micro-organism lacks a dihydrolipoamide transacetylase gene, or a portion of the dihydrolipoamide transacetylase gene has been deleted.

11. The micro-organism according to claim 1, wherein the amylase gene is derived from *Geobacillus stearothermophilus*.

12. The micro-organism according to claim 1, wherein the micro-organism is *Geobacillus thermoglucosidasius*.

13. The micro-organism according to claim 1, wherein the micro-organism does not comprise a restriction system.

14. The micro-organism according to claim 1, wherein the micro-organism is stable in a culture medium comprising up to 10% w/v ethanol.

15. The micro-organism according to claim 1, wherein the micro-organism grows at a temperature from 40° C.-85° C.

16. A method for the production of ethanol, comprising culturing a micro-organism in culture medium under suitable conditions in the presence of starch, wherein the micro-organism is a thermophilic micro-organism modified by the insertion of a heterologous amylase gene under the control of a suitable promoter, and further modified to inactivate the native lactate dehydrogenase (ldh) gene by deletion of the ldh gene or a portion thereof.

17. The method according to claim 16, wherein the culture medium comprises at least 10% w/v starch.

18. The method according to claim 16, wherein the method is carried out at a temperature of between 40° C.-70° C., and the micro-organism is maintained in culture at a pH of between 4 and 7.5.

19. An animal feed, comprising thermophilic micro-organisms modified by the insertion of a heterologous amylase gene under the control of a suitable promoter, and further modified to inactivate the native lactate dehydrogenase (ldh) gene by deletion of the ldh gene or a portion thereof.

* * * * *

SEQUENCE LISTING

```
<160> NUMBER OF SEQ ID NOS: 1

<210> SEQ ID NO 1
<211> LENGTH: 1654
<212> TYPE: DNA
<213> ORGANISM: Geobacillus stearothermophilus

<400> SEQUENCE: 1
ctaacgtttc accgcatcat tcgaaaagga tggatgttcc tgctcgcgtt tttgctcact      60
gccttgctgt tctgcccaac cggacagccc gccaaggctg ccgcaccgtt taacggcacc     120
atgatgcagt attttgaatg gtacttgccg gatgatggca cgttatggac caaagtggcc     180
aatgaagcca acaacttatc cagccttggc atcaccgctc tttggctgcc gcccgcttat     240
aaaggaacaa gccgcagcga cgtagggtac ggagtatacg acttgtatga cctcggtgaa     300
ttcaatcaaa aaggggccgt ccgcacaaaa tacgaaacaa aagctcaata tcttcaagcc     360
attcaagccg cccacgccgc tggaatgcaa gtgtacgccg atgtcgtgtt cgaccataaa     420
ggcggcgccg acgcacgga atgggtggac gccgtcgaag tcaatccgtc cgaccgcaac     480
caagaaatct cggcaccta tcaaatccaa gcatggacga aatttgattt tcccgggcgg     540
ggcaacacct actccagctt taagtggcgc tggtaccatt ttgatggcgt tgattgggac     600
gaaagccgaa aattgagccg catttacaaa ttccgcggca tcggcaaagc gtgggattgg     660
gaagtagaca cggaaaacgg aaactatgac tacttaatgt atgccgacct tgatatggat     720
catcccgaag tcgtgactga gctgaaaagc tgggggaaat ggtatgtcaa cacaacgaac     780
attgatgggt tccggcttga tgccgtcaag catattaagt tcagttttt tcctgattgg     840 ttgtcgtatg tgcgttctca gactggcaag ccgctattta ccgttgggga atattggagc     900
tataacatca acaagttgca caattacatt atgaaaacaa acggaacgat gtctttgttt     960
gatgccccgt tacacaacaa attttatacc gcttccaaat caggggcac atttgatatg    1020
```

```
cgcacgttaa tgaccaatac tctcatgaaa gatcaaccaa cattggccgt caccttcgtt    1080
gataatcatg acaccgaacc cggccaagcg ctgcagtcat gggtcgaccc atggttcaaa    1140
ccgttggctt acgcctttat tctaactcgg caggaaggat acccgtgcgt cttttatggt    1200
gactattatg gcattccaca atataacatt ccttcgctga aaagcaaaat cgatccgctc    1260
ctcatcgcgc gcagggatta tgcttacgga acgcaacatg attatcttga tcactccgac    1320
atcatcgggt ggacaaggga aggggtcact gaaaaaccag gatccggact ggccgcattg    1380
atcaccgatg ggccgggagg aagcaaatgg atgtacgttg gcaaacaaca cgccggaaaa    1440
gtgttctacg accttaccgg caaccggagt gacaccgtca ccatcaacag tgatggatgg    1500
ggggaattca aagtcaatgg cggttcggtt tcggtttggg ttcctagaaa aacgaccgtc    1560
tctactatcg cttggtcgat cacaacccga ccgtggactg atgaattcgt ccgttggacc    1620
gaaccacggt tggtggcatg gccttgatgc ctgc                                1654
```